(12) United States Patent
Edelman et al.

(10) Patent No.: US 7,658,205 B1
(45) Date of Patent: Feb. 9, 2010

(54) SYSTEMS FOR A FLUID CIRCUIT COUPLER

(75) Inventors: Howard Edelman, San Francisco, CA (US); Daqing Liu, Foster City, CA (US)

(73) Assignee: VitalWear, Inc., South San Francisco, CA (US)

( * ) Notice: Subject to any disclaimer, the term of this patent is extended or adjusted under 35 U.S.C. 154(b) by 0 days.

(21) Appl. No.: 11/676,921

(22) Filed: Feb. 20, 2007

Related U.S. Application Data (63) Continuation-in-part of application No. 10/326,714, filed on Dec. 19, 2002, now Pat. No. 7,191,798.

(51) Int. Cl.
*F16L 37/32* (2006.01)

(52) U.S. Cl. ................ 137/614.04; 137/594; 251/149.6

(58) Field of Classification Search ................ 137/614, 137/614.03, 614.04, 614.05, 594; 251/149.1, 251/149.6
See application file for complete search history.

(56) References Cited

U.S. PATENT DOCUMENTS

| | | | |
|---|---|---|---|
| 26,663 A | 1/1860 | French | |
| 128,220 A | * 6/1872 | Gardner et al. | 137/614.04 |
| 267,435 A | 11/1882 | Leiter | |
| 301,931 A | 7/1884 | Smith et al. | |
| 430,721 A | 6/1890 | Winkler | |
| 691,270 A | 1/1902 | Jones | |
| 787,920 A | 4/1905 | Hofmann | |
| 889,964 A | 9/1908 | Powell | |
| 1,817,277 A | 8/1931 | Uhlig | |
| 2,322,449 A | 6/1943 | Johnson et al. | |
| 2,451,218 A | * 10/1948 | Hengst | 137/614.04 |
| 2,504,569 A | 4/1950 | Murphy et al. | |
| 2,518,299 A | 8/1950 | Fernandez | |
| 2,666,656 A | 1/1954 | Bruning | |
| 2,726,658 A | 12/1955 | Chessey | |
| 2,773,531 A | 12/1956 | La Verne Johnson | |
| 2,896,977 A | 7/1959 | Hansen | |
| 2,911,974 A | 11/1959 | Spence | |
| 3,132,688 A | 5/1964 | Nowak | |
| 3,140,365 A | 7/1964 | Voland | |

(Continued)

FOREIGN PATENT DOCUMENTS

DE 3343664 3/1985

(Continued)

*Primary Examiner*—Kevin L Lee
(74) *Attorney, Agent, or Firm*—Kang S. Lim (57) ABSTRACT

The fluid coupler comprises a male coupler, a female coupler, and a seal between the male coupler and the female coupler when they are coupled, preventing fluid leakage. The female coupler receives the male coupler when in a coupled position. The male coupler includes a two pieced housing, a unitary valve and a biasing member. The two pieces of the housing may be joined. A cavity runs the length of the housing. The female coupler includes a housing, an annulus, a unitary valve and a biasing member. The annulus and the housing may be joined. A cavity runs the length of the housing. The unitary valves and biasing members fit within the cavities and are capable of longitudinal positioning within a configurable range. When male coupler and female coupler are coupled, the unitary valves are open permitting fluid flow. Otherwise, if uncoupled, the unitary valves are closed preventing fluid leakage.

16 Claims, 10 Drawing Sheets

U.S. PATENT DOCUMENTS

| | | | |
|---|---|---|---|
| 3,191,972 A | 6/1965 | Collar | |
| 3,283,780 A | 11/1966 | Sutton | |
| 3,284,842 A | 11/1966 | Jennings, Jr. | |
| 3,460,801 A | 8/1969 | Norton | |
| 3,548,819 A | 12/1970 | Davis et al. | |
| 3,556,470 A * | 1/1971 | Ehrens et al. | 251/149.4 |
| 3,586,048 A | 6/1971 | Arnold | |
| 3,612,059 A | 10/1971 | Ersek | |
| 3,648,765 A | 3/1972 | Starr | |
| 3,683,902 A | 8/1972 | Artemenko et al. | |
| 3,687,161 A * | 8/1972 | Grguric et al. | 137/614.05 |
| 3,744,555 A | 7/1973 | Fletcher et al. | |
| 3,788,348 A | 1/1974 | Johnson | |
| 3,869,871 A | 3/1975 | Rybalko et al. | |
| 3,871,381 A | 3/1975 | Roslonski | |
| 3,886,936 A | 6/1975 | Wehrenberg | |
| 3,901,225 A | 8/1975 | Sconce | |
| 3,916,929 A | 11/1975 | Brown | |
| 3,993,053 A | 11/1976 | Grossan | |
| 3,995,621 A | 12/1976 | Fletcher et al. | |
| 4,099,522 A | 7/1978 | Alenares | |
| 4,149,529 A | 4/1979 | Copeland et al. | |
| 4,149,541 A | 4/1979 | Gammons et al. | |
| 4,184,537 A | 1/1980 | Sauder | |
| 4,196,772 A | 4/1980 | Adamski et al. | |
| 4,200,121 A * | 4/1980 | Walter et al. | 137/614.05 |
| 4,273,290 A | 6/1981 | Quinn | |
| 4,338,944 A | 7/1982 | Arkans | |
| 4,459,468 A | 7/1984 | Bailey | |
| 4,552,132 A | 11/1985 | Ruscigno | |
| 4,587,959 A | 5/1986 | Ruderian | |
| 4,669,476 A | 6/1987 | Gordon et al. | |
| 4,691,762 A | 9/1987 | Elkins et al. | |
| 4,703,957 A | 11/1987 | Blenkush | |
| 4,733,692 A | 3/1988 | Kotake et al. | |
| 4,823,651 A * | 4/1989 | England | 81/124.4 |
| 4,844,072 A | 7/1989 | French et al. | |
| 4,846,176 A | 7/1989 | Golden | |
| 4,877,181 A | 10/1989 | Stewart | |
| 4,910,978 A | 3/1990 | Gordon et al. | |
| 4,913,316 A * | 4/1990 | Richter | 222/1 |
| 4,962,761 A | 10/1990 | Golden | |
| 4,989,790 A | 2/1991 | Martin et al. | |
| 5,013,013 A | 5/1991 | Spedding | |
| 5,038,852 A | 8/1991 | Johnson et al. | |
| 5,051,562 A | 9/1991 | Bailey et al. | |
| 5,072,875 A | 12/1991 | Zacoi | |
| 5,077,980 A | 1/1992 | Weber | |
| 5,080,089 A | 1/1992 | Mason et al. | |
| 5,086,771 A | 2/1992 | Molloy | |
| 5,143,064 A | 9/1992 | Cochran | |
| D331,115 S | 11/1992 | Stout | |
| D333,350 S | 2/1993 | Redira, Jr. | |
| 5,183,039 A | 2/1993 | Sarian et al. | |
| 5,230,335 A | 7/1993 | Johnson, Jr. et al. | |
| 5,232,020 A * | 8/1993 | Mason et al. | 137/614.04 |
| 5,234,166 A | 8/1993 | Foster et al. | |
| D344,343 S | 2/1994 | McNew | |
| 5,314,455 A | 5/1994 | Johnson, Jr. et al. | |
| 5,316,041 A | 5/1994 | Ramacier, Jr. et al. | |
| 5,324,318 A | 6/1994 | Smith | |
| 5,324,319 A | 6/1994 | Mason et al. | |
| 5,330,519 A | 7/1994 | Mason et al. | |
| 5,344,436 A | 9/1994 | Fontenot et al. | |
| 5,368,234 A | 11/1994 | Foster et al. | |
| 5,372,608 A | 12/1994 | Johnson | |
| 5,383,919 A | 1/1995 | Kelly et al. | |
| 5,386,823 A | 2/1995 | Chen | |
| D358,216 S | 5/1995 | Dye | |
| 5,411,541 A | 5/1995 | Bell et al. | |
| 5,417,720 A | 5/1995 | Mason | |
| 5,433,083 A | 7/1995 | Kuramarohit | |
| 5,439,473 A | 8/1995 | Jorgensen | |
| 5,441,533 A | 8/1995 | Johnson et al. | |
| 5,449,379 A | 9/1995 | Hadtke | |
| 5,456,701 A | 10/1995 | Stout | |
| 5,466,250 A | 11/1995 | Johnson, Jr. et al. | |
| 5,466,251 A | 11/1995 | Brunson et al. | |
| 5,476,489 A | 12/1995 | Koewler | |
| 5,486,207 A | 1/1996 | Mahawili | |
| 5,499,766 A | 3/1996 | Foster et al. | |
| 5,507,792 A | 4/1996 | Mason et al. | |
| D369,866 S | 5/1996 | Baughn | |
| 5,555,579 A | 9/1996 | Wu | |
| 5,562,604 A | 10/1996 | Yablon et al. | |
| 5,603,728 A | 2/1997 | Pachys | |
| 5,617,811 A | 4/1997 | Johnson | |
| 5,647,051 A | 7/1997 | Neer | |
| 5,662,695 A | 9/1997 | Mason et al. | |
| 5,668,565 A | 9/1997 | Robinson | |
| 5,711,155 A | 1/1998 | DeVilbiss et al. | |
| RE35,744 E | 3/1998 | Foster et al. | |
| D393,719 S | 4/1998 | Nichols | |
| 5,741,220 A | 4/1998 | Brink | |
| 5,755,275 A | 5/1998 | Rose et al. | |
| 5,755,733 A | 5/1998 | Morita | |
| 5,755,755 A | 5/1998 | Panyard | |
| 5,865,841 A | 2/1999 | Kolen et al. | |
| 5,891,188 A | 4/1999 | Maytal | |
| 5,894,615 A | 4/1999 | Alexander | |
| 5,904,291 A | 5/1999 | Knapp | |
| 5,968,072 A | 10/1999 | Hite et al. | |
| 6,050,297 A | 4/2000 | Ostrowski et al. | |
| 6,117,164 A | 9/2000 | Gildersleeve et al. | |
| 6,149,617 A | 11/2000 | McNally et al. | |
| 6,270,055 B1 | 8/2001 | Szeteli et al. | |
| 6,295,819 B1 | 10/2001 | Mathiprakasam et al. | |
| 6,299,626 B1 | 10/2001 | Viranyi | |
| 6,352,550 B1 | 3/2002 | Gildersleeve et al. | |
| 6,440,159 B1 | 8/2002 | Edwards et al. | |
| 6,551,347 B1 | 4/2003 | Elkins | |
| 6,699,267 B2 | 3/2004 | Voorhees et al. | |
| 6,827,728 B2 | 12/2004 | Ellingboe et al. | |
| 6,957,697 B2 | 10/2005 | Chambers | |
| 7,000,682 B2 | 2/2006 | Chambers | |
| 7,191,798 B2 | 3/2007 | Edelman et al. | |
| 7,211,104 B2 | 5/2007 | Edelman | |
| 2001/0018604 A1 | 8/2001 | Elkins | |
| 2001/0039439 A1 | 11/2001 | Elkins et al. | |
| 2002/0019657 A1 | 2/2002 | Elkins | |
| 2002/0026226 A1 | 2/2002 | Ein | |
| 2002/0032473 A1 | 3/2002 | Kushnir et al. | |
| 2004/0068310 A1 | 4/2004 | Edelman | |

FOREIGN PATENT DOCUMENTS

| | | |
|---|---|---|
| DE | 3410413 | 10/1985 |
| GB | 2 175 496 A | 12/1986 |
| IT | 246899 | 3/1926 |
| SU | 577-350 | 10/1977 |

* cited by examiner

SYSTEMS FOR A FLUID CIRCUIT COUPLER

CROSS REFERENCE TO RELATED APPLICATIONS

This is a continuation-in-part of U.S. application Ser. No. 10/326,714 filed on Dec. 19, 2002, now U.S. Pat. No. 7,191,798, and entitled "Fluid Circuit Connector System", which is hereby fully incorporated by reference.

BACKGROUND OF THE INVENTION

The present invention relates generally to fluid circuit connector systems. More specifically, the invention concerns quick-release connectors having couplers with single part unitary valves for controlling fluid leakage.

Fluid circuits are useful in a variety of contexts, particularly providing hot and/or cold therapeutic treatments to sore body parts. The potential effectiveness of a hot or cold treatment increases with the level of temperature control. Precise temperature control can be achieved through a carefully controlled fluid circuit. Fluids have a high rate of heat transfer and the precise temperature may be quickly changed and easily maintained. Examples of devices for delivering hot or cold fluids for therapeutic purposes include United States Patent Publication Number 2001/0039439 A1 to Elkins and U.S. patent application Ser. No. 10/267,247 filed on Oct. 8, 2002, and entitled "Contrast Therapy System and Method", both of which are incorporated herein by reference.

Therapy devices configured to deliver hot and cold treatments may employ one or more reservoirs of fluid. Often these devices include one hot fluid reservoir and one cold fluid reservoir configured to connect via a fluid circuit to a therapy pad or wrap. The therapy pad or wrap may be configured to fit a specific part of the body. For example, wraps are often designed to apply therapy to a limb, such as an arm or a leg, and pads are often designed to apply therapy to the torso, particularly the back or shoulders.

It may be desirable to easily interchange between wraps or pads of varying capacity and size. Additionally, it may be desirable to eliminate fluid loss such as to reduce mess, the need to refill reservoirs, and to ensure that sore body parts remain dry which is of particular importance when soreness is due to wound or post operative healing.

It is therefore apparent that an urgent need exists for an improved fluid circuit connector system that enables rapid interchangeability, while eliminating leakage.

SUMMARY OF THE INVENTION

To achieve the foregoing and in accordance with the present invention, a system for a fluid circuit coupler is provided. Such a system is useful for a system that supplies fluids for any purpose. In some embodiments, such a system may be useful in delivering hot and/or cold fluids for therapy for sore or damaged body parts.

One advantage of the present invention is that the fluid coupler enables rapid coupling and decoupling of portions of a fluid circuit while preventing leakage. The fluid coupler comprises a male coupler, a female coupler, and a seal positioned between the male coupler and the female coupler when they are coupled, thereby preventing fluid from leaking out from the coupled fluid coupler. The female coupler receives the male coupler when in a coupled position.

The male coupler includes a two pieced housing, a unitary valve and a biasing member. The two pieces of the housing may be joined via welding, threading, glue or compression fitting. A cavity runs the length of the housing. The unitary valve and biasing member fit within the cavity and are capable of longitudinal positioning within a configurable range. The unitary valve includes a sealer, which seals the male coupler when it is decoupled from the female coupler.

The female coupler includes a housing, an annulus, a unitary valve and a biasing member. The annulus and the housing may be joined via welding, threading, glue or compression fitting. A cavity runs the length of the housing. The unitary valve and biasing member fit within the cavity and are capable of longitudinal positioning within a configurable range. The unitary valve includes a sealer, which seals the female coupler when it is decoupled from the male coupler.

The fluid coupler is configured to be in one of a coupled position and an uncoupled position. When in the coupled position, the unitary valves are open permitting fluid flow through the coupler. Otherwise, when in the uncoupled position the unitary valves are closed preventing fluid leakage.

These and other features of the present invention will be described in more detail below in the detailed description of the invention and in conjunction with the following figures.

BRIEF DESCRIPTION OF THE DRAWINGS

In order that the present invention may be more clearly ascertained, one embodiment will now be described, by way of example, with reference to the accompanying drawings, in which.

DETAILED DESCRIPTION OF THE INVENTION

The present invention will now be described in detail with reference to several embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention. The features and advantages of the present invention may be better understood with reference to the drawings and discussions that follow.

Figure 1:
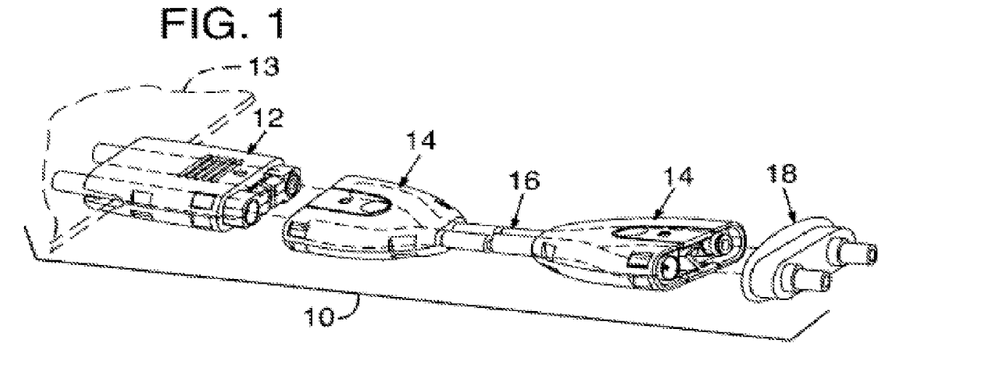
FIG. 1 shows a perspective view of an embodiment of a fluid circuit connector system according to the present invention.

To facilitate discussion, FIG. 1 shows a fluid circuit connection system, indicated generally at 10. Although useful for a variety of fluid circuit systems, the illustrated embodiment is shown in the context of a contrast therapy wrap. Fluid circuit connection system 10 includes an object fitting 12, as shown the object fitting is connected to a contrast therapy applicator 13, such as a pad or wrap. Contrast therapy applicator 13 may be any of a variety of contrast therapy applicators including arm wraps, leg wraps, waist wraps, shoulder wraps, and pads for applying therapy to various sore body parts. Object fitting 12 may be configured to receive a quick-release connector 14 attached to one end of a set of tubes 16. At the other end of tube set 16 is another quick-release connector 14 configured to connect to a source fitting 18. Source fitting 18 connects the fluid circuit to a source of hot and cold fluid for circulation.

It will be understood that in the illustrated embodiment both quick-release connectors 14 may be used to attach to either object fitting 12 or source fitting 18. Other embodiments of the present invention may have quick-release connectors 14 that may be fitting specific. For example, a quick-release connector configured to attach to object fitting 12 may not connect to source fitting 18 and vice versa. This may be desirable for enabling the use of a contrast therapy fluid supply with a variety of therapy wraps and pads that may have different types and or sizes of object fittings.

Figure 2:
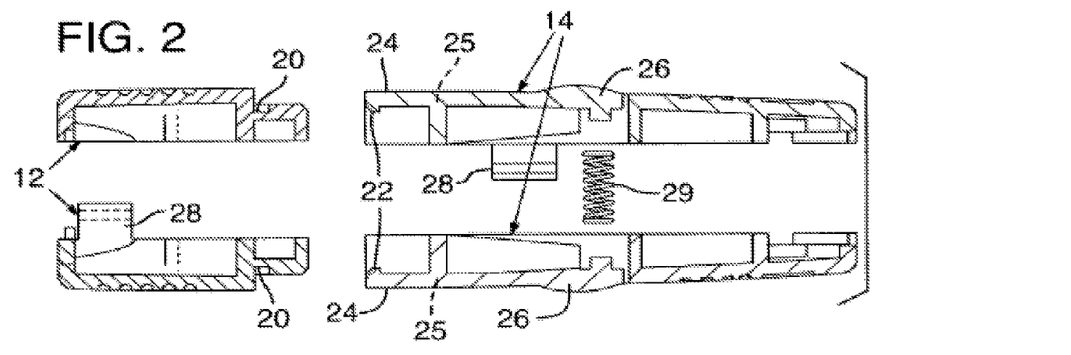
FIG. 2 shows an exploded and sectioned side view of an embodiment of a quick-release connector for use with the fluid circuit connector system of FIG. 1.
Figure 3:
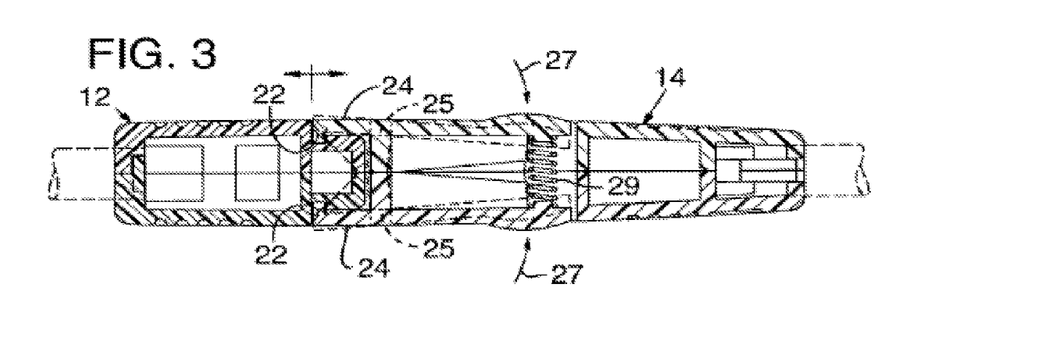
FIG. 3 shows a sectional side view of the quick-release connector of FIG. 2, shown in a connected configuration.

FIGS. 2 and 3 show the latch operation of object fitting 12 and quick-release connector 14. Object fitting 12 includes latch recesses 20 configured to receive latch tabs 22 from quick-release connector 14. Latch tabs 22 may be positioned at the ends of latch arms 24 of quick-release connector 14. Latch arms 24 may be attached to connector 14 at a thinned rotational flex point 25. Latch release buttons 26 may be attached to quick-release connector 14 on an opposed side of flex point 25 from latch arms 24. Latch buttons 26 are biased outward by a biasing member 29. The outward bias of latch buttons 26 causes a slight inward bias to latch arms 24 on the opposite side of flex point 25.

Quick-release connector 14 may be connected to object fitting 12 by depressing latch buttons 26 with a squeezing motion, as illustrated in FIG. 3, by arrows 27. Depressing latch buttons 26 causes latch arms 24 to spread out, as illustrated in dashed lines in FIG. 3. With latch buttons 26 depressed, quick-release connector 14 may be pushed into engagement with object fitting 12. Once quick latch 14 is pushed into engagement, latch buttons 26 may be released causing spring 29 to urge latch arms 24 to close together and latch tabs 22 to engage latch recesses 20, thus securing connector 14 to fitting 12.

As shown in FIG. 2, object fitting 12 and quick latch connector 14 may be made of two halves that are held together with snap fittings 28. Pressing each half together around the tubes and couplers carrying fluid to the object or from the object completes the fitting and connector. Other constructions for object fitting 12 and quick-release connector 14 may also be used.

Releasing quick-release connector 14 may be accomplished by simply reversing the above process. First, depress latch buttons 26 spreading latch arms 24 and causing latch tabs 22 to release from latch recesses 20. Second, pull quick-release connector 14 from object fitting 12.

Source fitting 18 similarly includes latch recesses configured to receive latch tabs 22 of quick lock connector 14. Therefore, quick-release connector 14, which is attached to the other end of tube set 16, may be connected to and released from source fitting 18 in the same manner as described with regard to object fitting 12. It will be understood that both quick-release connectors 14 are constructed in the same manner and may be used to attach to either object fitting 12 or source fitting 18.

Figure 4:
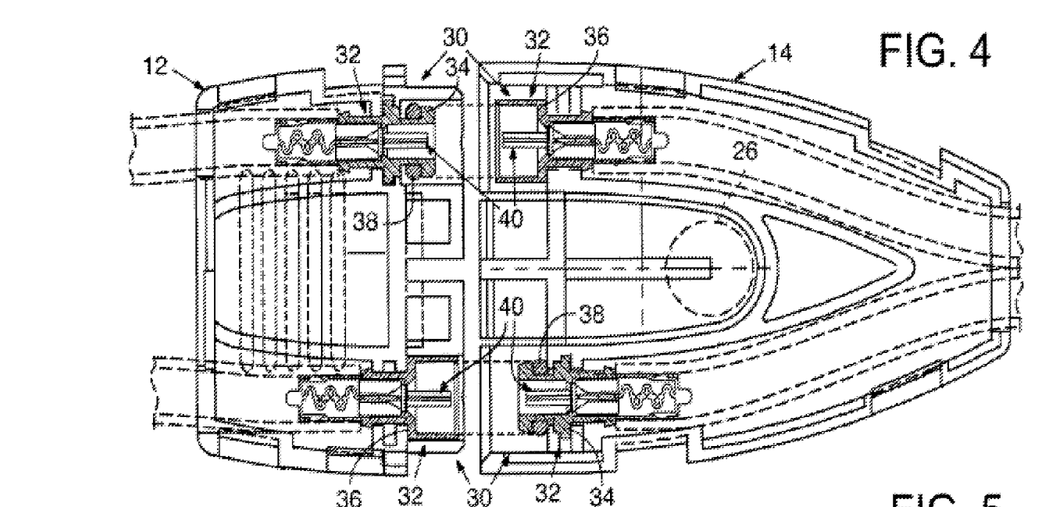
FIG. 4 shows a partially sectioned top view of an embodiment of a quick-release connector of the present invention showing a disconnected configuration.

FIG. 4 shows object fitting 12 and quick-release connector 14 in a disconnected configuration. Object fitting 12 and quick-release connector 14 may each include two halves of a fluid coupler 30. Fluid coupler 30 is a device configured to permit the ends of two tubes to couple in fluid communication with one another and to seal the ends of the two tubes upon decoupling.

Each fluid coupler includes a pair of coupler housings 32. Coupler housings 32 may include two types. A male coupler housing 34 may be configured for insertion into a female housing 36. Object fitting 12 may include one of each type of housing, as shown in FIG. 4, or may include two of the same types of coupler housings. It will be understood that, if object fitting 12 has one of each type of coupler housing, then in a corresponding location quick-release connector 14 must have the complementary coupler housing type. For example, as shown in FIG. 4, object fitting 12 includes male coupler housing 34 in a top location and female coupler housing 36 in a bottom location, therefore quick-release connector 14 should have female coupler housing 36 in a top location and male coupler housing 34 in a bottom location.

Fluid coupler 30 may include a seal 38 to prevent fluid from escaping between male coupler housing 34 and female coupler housing 36. Seal 38 may be an O-ring type seal that is configured to sit in place in a groove cut in male housing 36. It will be understood that seal 38 may include other suitable sealing gaskets or mechanisms and may be configured to sit in place in either the male of female coupler housing.

In operation, quick-release connector 14 and object fitting 12, or source fitting 18, will fully latch prior to male coupler housing 34 and female coupler housing 36 bottoming out against one another. This ensures that the quick-lock connector engages properly and prevents the coupler housings from interfering with a proper latch between quick-lock connector 14 and one of the fittings.

Each coupler housing 32 includes a valve assembly. It follows that each fluid coupler 30 then includes two valve assemblies. A valve assembly may be configured to open a fluid flow path between two tube ends. Tubes may be press fit over the ends of coupler housings 32 to enable fluid communication between the tubes and the fluid coupler.

Figure 5:
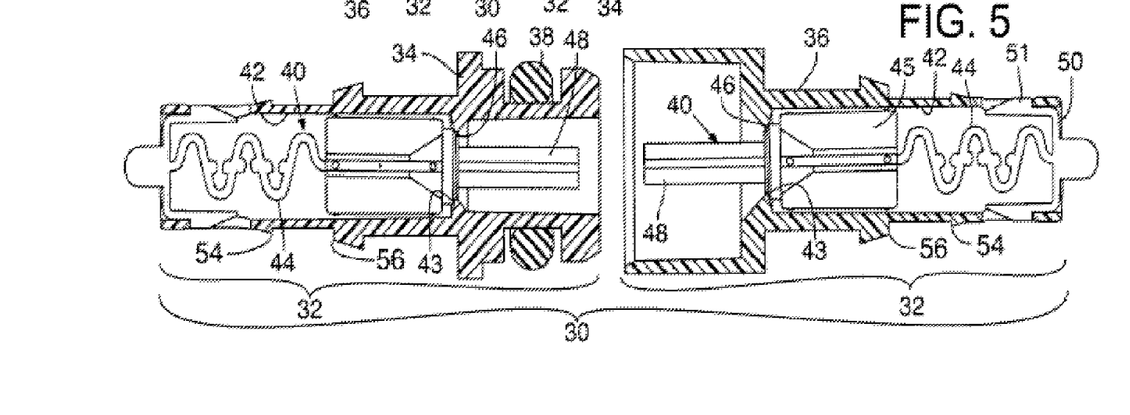
FIG. 5 shows a partially sectioned side view of a fluid coupler according to an embodiment of the present invention, shown in a disconnected and closed configuration.

FIG. 5 illustrates a decoupled fluid coupler 30. Fluid coupler 30 may include two main components, namely coupler housings 32 and unitary valve 40. The combination of portions of coupler housing 32 and unitary valve 40 may be referred to as a valve assembly. Unitary valve 40 cooperates with a housing seat 43 in housing 32 to seal off one section of housing 32 from another section. Housing seat 43 may be formed integral with coupler housing 32. Unitary valve 40 may be configured to fit within coupler housing 32. For example, coupler housing 32 may include an elongate bore 42 adapted to receive unitary valve 40 axially within elongate bore 42. Housing seat 43 may be positioned within elongate bore 42 of coupler housing 32.

Unitary valve 40 may include a biasing member 44 configured to bias the unitary valve into engagement with housing seat 43. Unitary valve 40 may include a stabilizer 45 formed integral with biasing member 44 and configured to aid in the alignment of valve assembly 40. A valve seat surface 46 may be formed integral with stabilizer 45 and biasing member 44 and configured to engage housing seat 43 to close unitary valve 40 and prevent leakage from the end of a tube connected therewith. Unitary valve 40 further includes a valve stem 48 formed integral with valve seat 46, stabilizer 45, and biasing member 44. Valve stem 48 may be configured to receive a force opposing biasing member 44 to open unitary valve 40, as will be explained in detail below.

Unitary valve 40 may include a retainer 50 configured to hold the unitary valve within fluid coupler housing 32. Retainer 50 may include retainer prongs 51. Fluid coupler housing 32 may include retainer detents 52 configured to receive retainer prongs 51 of retainer 50 and secure unitary valve 40 inside bore 42 of fluid coupler housing 32.

Coupler housings 32 may include a barb 54 positioned near one end of each coupler housing and configured to aid in retaining a press fit tube that has been pressed onto the coupler housing. Each housing may also include a flange 56 configured to limit the distance that a press fit tube may extend over coupler housing 32. A tube is fully press fit when the end of the tube abuts flange 56. In the depicted embodiment, the tube seals off retainer detents 52 preventing fluid from escaping from these openings. It will be understood that this sealing function may not occur if detents 52 do not open up to the outside of housing 32.

As depicted in FIG. 5, fluid coupler 30 is in a decoupled configuration. In the decoupled configuration valve seat 46 engages with housing seat 43 to block the flow of fluid out of the end of coupler housing 32. Biasing member 44 applies a biasing force to valve seat 46 through stabilizer 45 to press valve seat 46 into housing seat 43 and seal the valve. Stabilizer 45 along with valve guides 60 act to limit the misalignment of unitary valve 40 with respect to bore 42 of coupler housing 32. Valve stem 48 extends toward a coupling end of coupler housing 32 and is configured to cause the valve to open when valve stem 48 is engaged and pressed reward in the coupler housing by opposing valve stem 48.

Figures 6, 7:
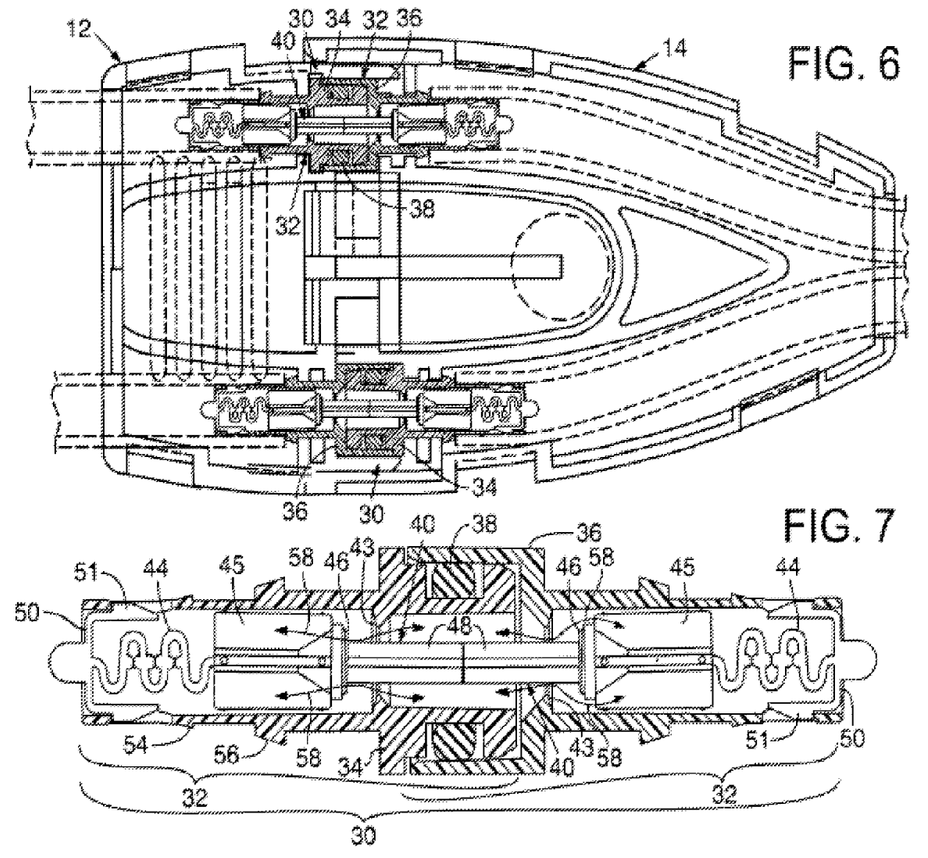
FIG. 6 shows a partially sectioned top view of the quick-release connector of FIG. 4, shown in a connected configuration.
FIG. 7 shows a partially sectioned side view of the fluid coupler of FIG. 5, shown in a connected and open configuration.

FIG. 6 depicts object fitting 12 and quick-release connector 14 in a connected configuration. In the connected configuration each fluid coupler is coupled and configured to permit fluid to flow through the coupler. A detailed view of the fluid coupler, illustrated uncoupled in FIG. 5, is shown in a coupled configuration in FIG. 7. Flow arrows 58 illustrate the fluid flow path through the coupled fluid coupler 30.

In the coupled fluid coupler of FIG. 7, the coupling end of male housing 34 slides into the coupling end of female housing 36. Initially, as the two housings 34 and 36 slide together, seal 38, which may be an O-ring type seal or any other suitable sealing member, engages and seals the coupling ends of the two housing to prevent fluid leaks. As the two housings 34 and 36 slide further together valve stems 48 of each coupler housing 32 engage one another causing the two biasing members 44 to compress. Compressing biasing members 44 permits the rest of unitary valves 40 to slide away from the coupling ends of coupling housings 32. As unitary valve 40 slides away from the coupling end of coupling housing 32, valve seat 46 separates from housing seat 43 opening a path for fluid to flow through, as illustrated by flow arrows 58. It will be understood that seal 38 seals the two housings prior to either unitary valve opening.

Figure 8:
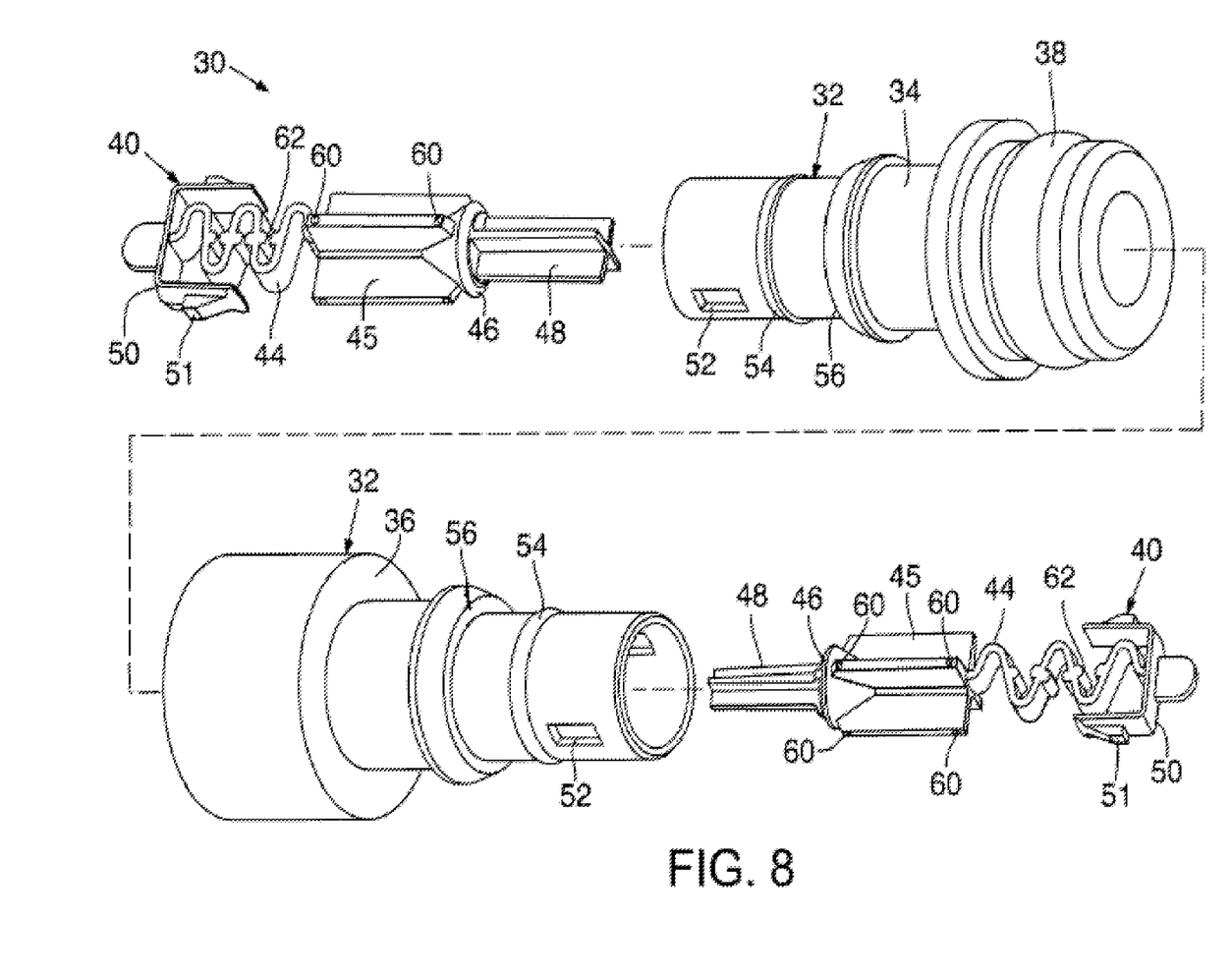
FIG. 8 shows an exploded assembly view of the fluid coupler of FIGS. 5 and 7.

FIG. 8 illustrates the assembly of unitary valves 40, male coupler housing 34, and female coupler housing 36. Valve stem 48 includes an X-shaped cross section, which allows opposed valve stems to engage as intended with an increased amount of misalignment between the opposed valve stems while maintaining an adequate flow passage. While valve stem 48 is shown with an X-shaped cross section it will be understood that other embodiments may employ other shapes.

As noted above, stabilizer 45 includes a series of radial fins extending radically from a central region. Stabilizer 45 includes a plurality of valve guides 60 positioned on the ends of fins and configured to engage the interior wall of bore 42 in coupler housing 32. Engaging the interior wall of bore 42 in coupler housing 32 provides an alignment function for unitary valve 40. The geometry of stabilizer 45 may be configured to provide a stabilizing function to the unitary valve, while minimizing the interference with fluid flow when the valve assembly is open.

In the depicted embodiment biasing member 44 of unitary valve 40 is a ribbon spring. Each ribbon spring may include a set of compression limits 62. Compression limits 62 prevent either one of the ribbon springs in a coupler from being over compressed preventing the opposing valve from opening. For example, if one ribbon spring is less stiff than the opposing spring it will bottoms out on compression limits 62 first and the other spring will begin to compress as housings 34 and 36 are pressed further together. In this way, the other valve will fully unseat and open a flow path before male housing 34 is completely inserted into female housing 36. Other configurations for biasing member 44 may be used including a coil type spring, an elastic member, or other structure capable of biasing the unitary valve.

Unitary valve 40 may be inserted into bore 42 in a tube-attaching end 63 of coupler housing 32. When unitary valve 40 is fully inserted and the ribbon spring preloaded, retainer detents 52, positioned close to tube-attaching end 63, may be configured to receive retainer prong 51 extending from retainer 50. This configuration holds the unitary valve in place inside the coupler housing. This process applies to both the male coupler housing and the female coupler housing.

Figures 9, 10:
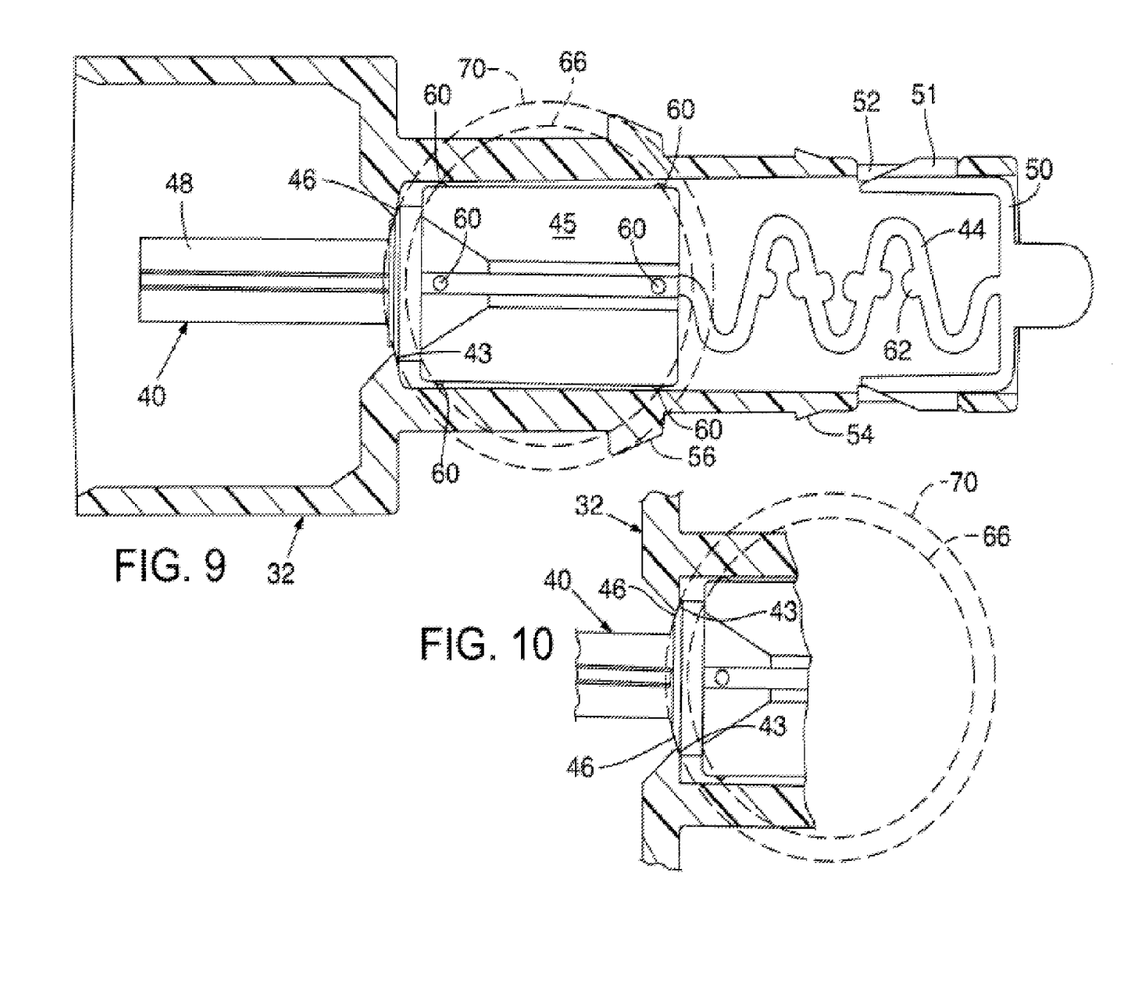
FIG. 9 shows a partially sectioned side view of a fluid coupler housing and a unitary valve illustrating concentric spherical radii, which define the relative position of a valve seat and a set of valve guides.
FIG. 10 shows an enlarged view of FIG. 9, showing a partially sectioned a cut away view of the valve seat and housing seat of and embodiment of the present invention.

FIG. 9 illustrates the misalignment interaction between coupler housing 32 and valve guides 60. Semispherical valve guides 60 are positioned on stabilizer 45, such that those points of valve guides 60 where contact with bore 42 may occur all lie on a theoretical valve guide spherical surface 66. Valve seat 46 includes a spherical surface that lies in theoretical spherical surface 70a that is concentric with theoretical valve guide spherical surface 66. Valve assembly 40 may function properly with larger tolerances between bore 42 of coupler housing 32 and valve guides 60 because of the concentric configuration of the contact points of valve guides 60 and valve seat surface, which lies in theoretical spherical surface 70a.

For example, a misalignment that causes two of the valve guides 60 to contact bore 42 of the coupler housing can occur simultaneously with the surface of valve seat 46 fully engaging housing seat 43, as illustrated in FIG. 10. That is to say, valve seat 46 will properly engage and prevent leakage even though unitary valve 40 is maximally misaligned, such misalignment being limited by one or more of valve guides 60 contacting the bore wall 42 of housing 32.

FIGS. 11A to 14 provide additional embodiments of the fluid coupler. Said additional embodiments of the fluid coupler differ in biasing member type, and method of biasing member retention. The housing of said additional embodiments is segmental in order to enable the reception of the biasing member. Said segmental housings provide for a more stable longitudinal movement of the biasing member and unitary valve within the housing, wherein the longitudinal axis of the unitary valve remains parallel to the longitudinal axis of movement when coupling and decoupling the coupler. Additionally, the helical coil geometry of the biasing member, such as a spring, aids in the stable longitudinal movement of the biasing member and unitary valve within the coupler housing. Said stability of movement thus results in a more flush seal between unitary valve seal and the housing when the coupler is decoupled. This more robust seal of the unitary valve seal thus results in a reduction of leaks. Moreover, this design provides for fewer failures over prior art.

Figure 11A:
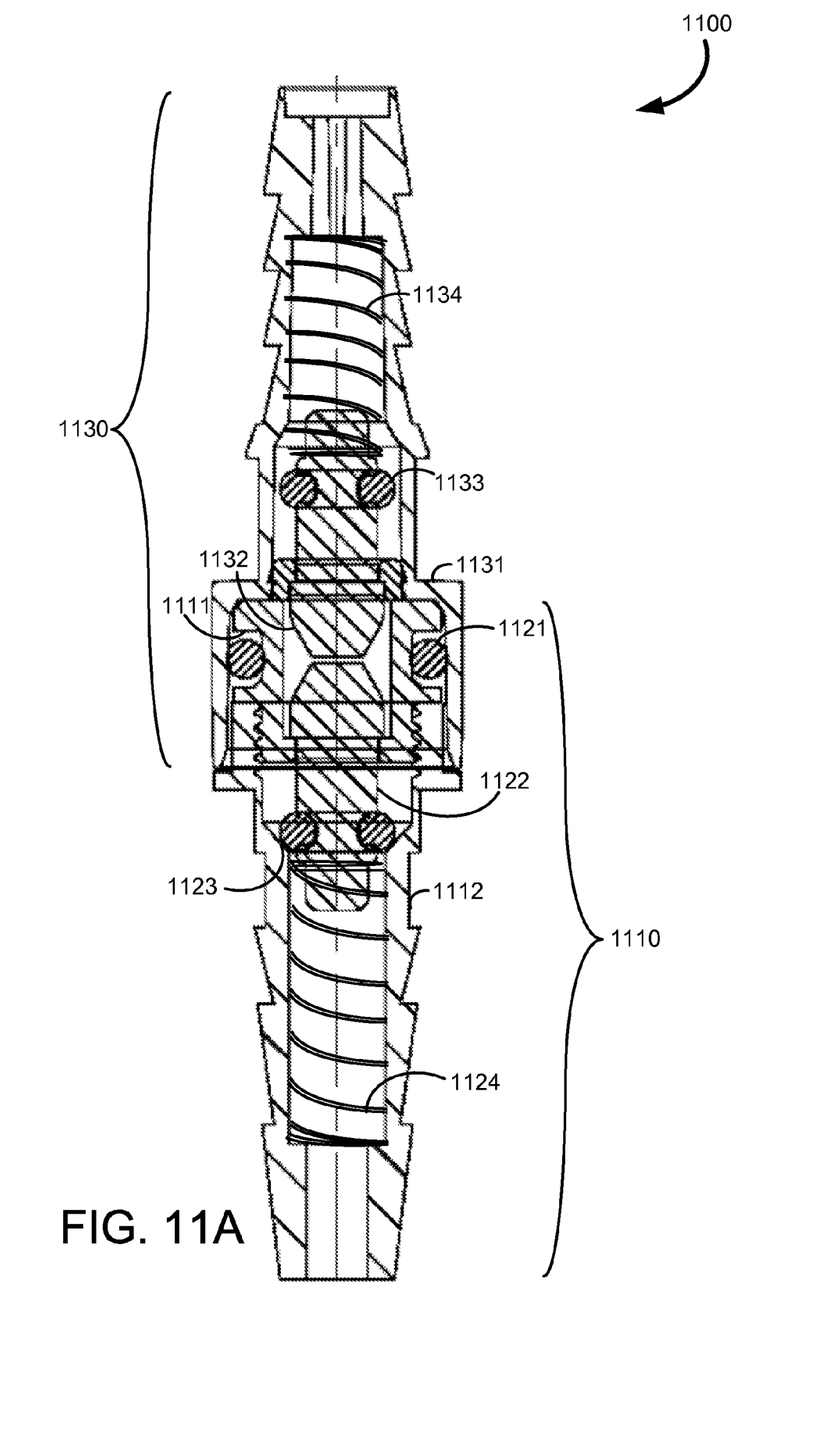
FIG. 11A shows a partially sectioned side view of the fluid coupler shown in a connected and open configuration, in accordance with an embodiment of the present invention.
Figure 11B:
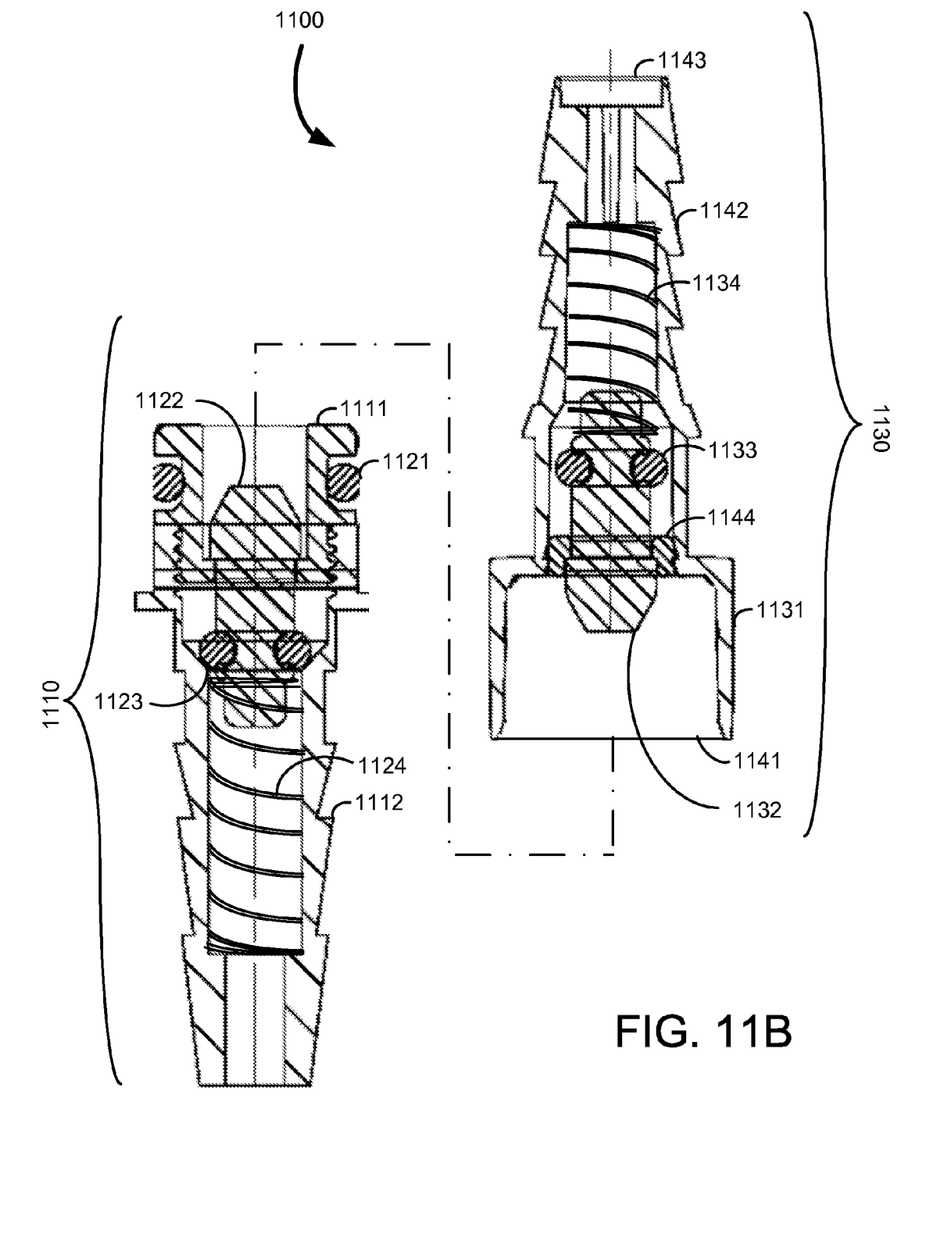
FIG. 11B shows a partially sectioned side view of the fluid coupler of FIG. 11A, shown in a disconnected configuration.
Figure 12:
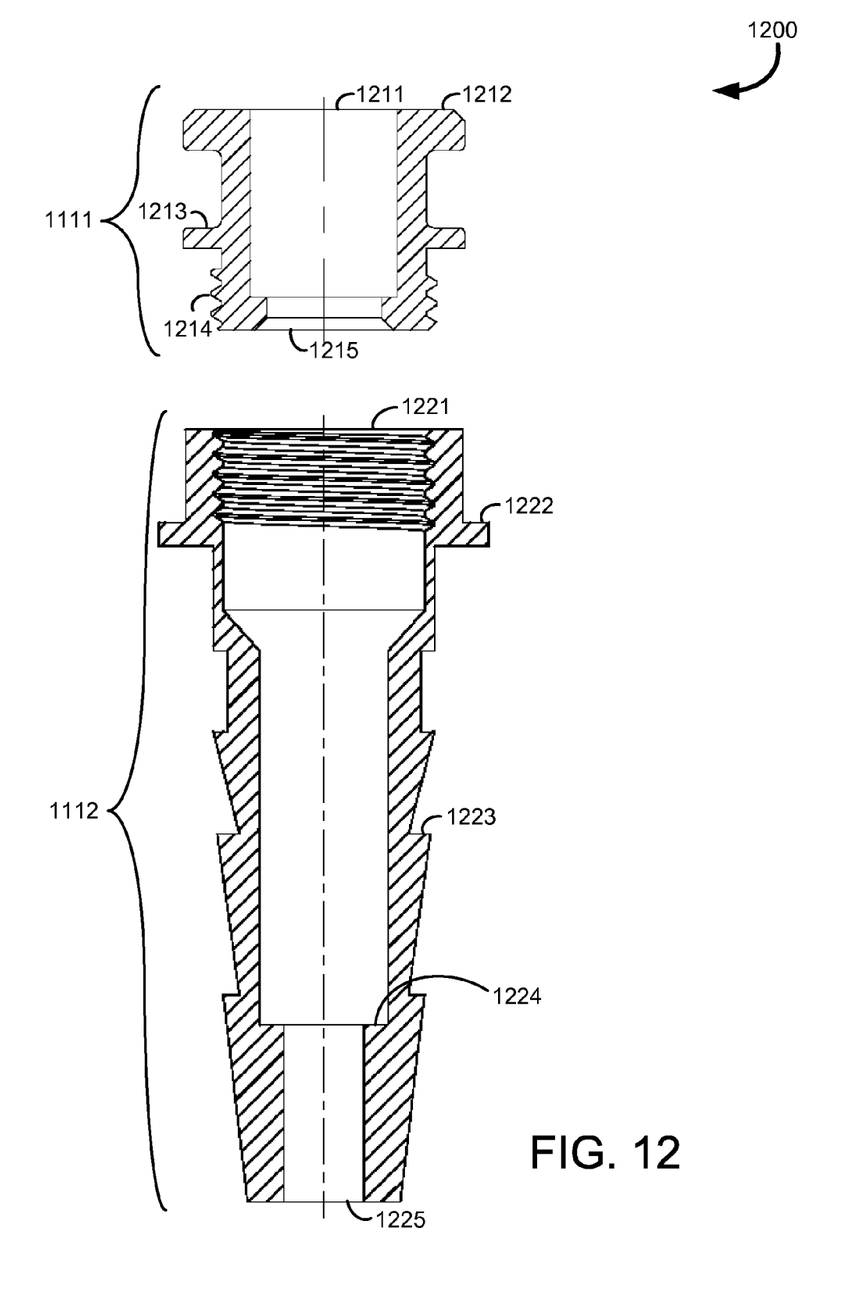
FIG. 12 shows a partially sectioned side view of a male fluid coupler housing according to an embodiment of the present invention.
Figure 13:
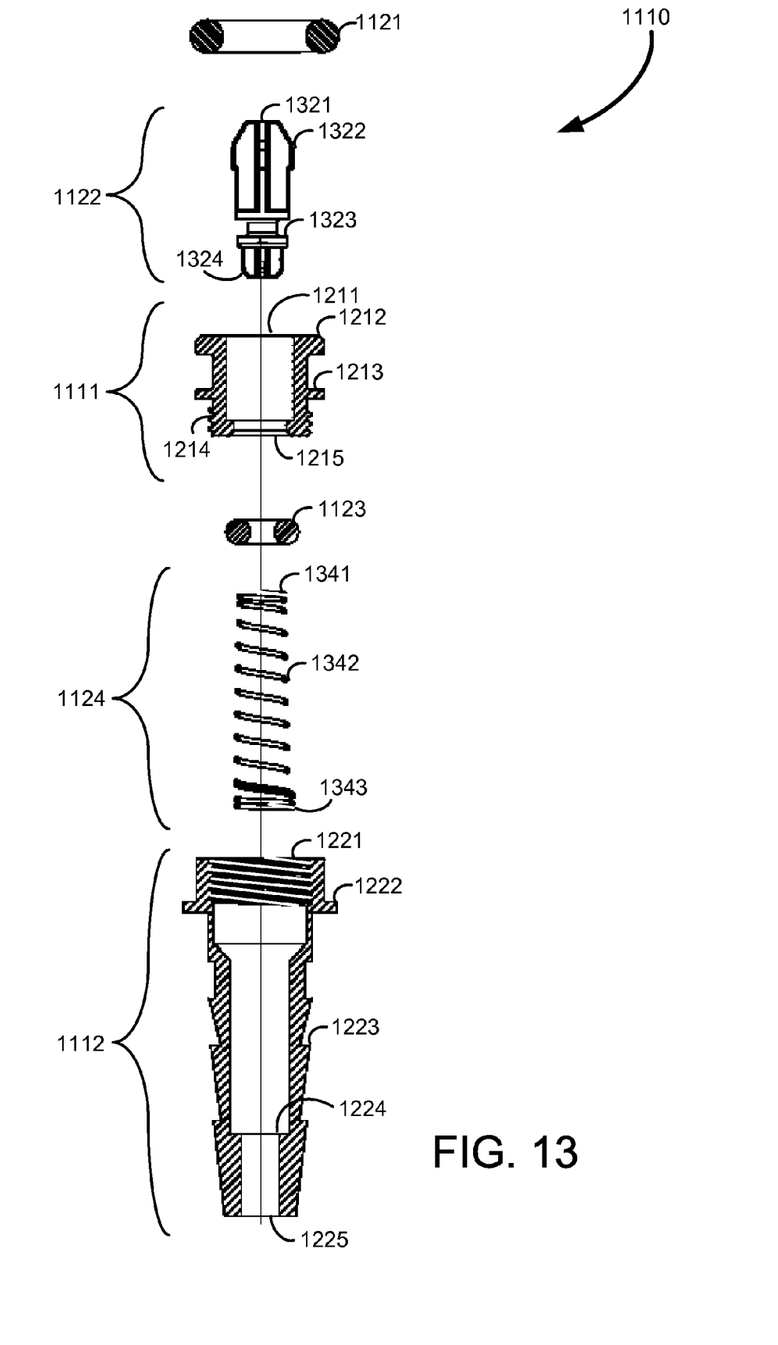
FIG. 13 shows an exploded assembly view of the male fluid coupler according to an embodiment of the present invention.
Figure 14:
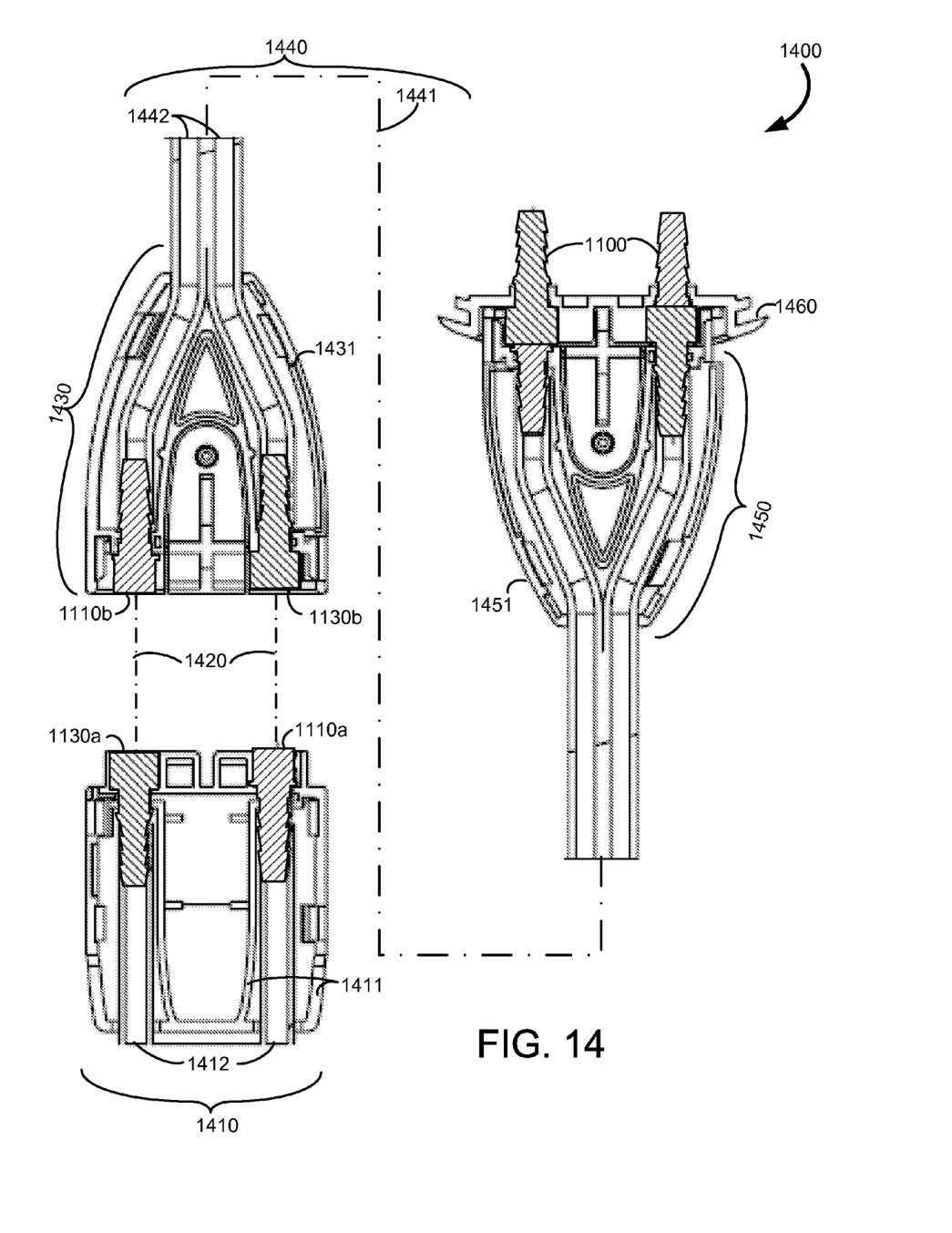
FIG. 14 shows a sectional side view of the quick-release connector including the fluid coupler of FIG. 11A, according to an embodiment of the present invention.

FIG. 11A provides a cross sectional illustration of said additional embodiments of the fluid coupler, wherein the male and female couplers are coupled. FIG. 11B, similarly, provides a cross sectional illustration of said additional embodiments of the fluid coupler, however here the male and female couplers are decoupled. FIG. 12 illustrates in greater detail the segmented housing of the male coupler. FIG. 13 illustrates an exploded cross sectional view of the male coupler. Lastly, FIG. 14 illustrates the couplers of FIGS. 11A and 11B incorporated within an exemplary fluid circuit. Below is a more detailed description of the FIGS. 11A to 14.

FIG. 11A shows a partially sectioned side view of a Joined Fluid Coupler 1100, shown in a connected and open configuration, in accordance with an embodiment of the invention. In some embodiments, a Male Fluid Coupler 1110 may couple with a Female Fluid Coupler 1130. In the connected configuration each fluid coupler is coupled and configured to permit fluid to flow through the Joined Fluid Coupler 1100. A Male Fluid Coupler Housing Top 1111 may be inserted into a Receptacle 1141 of the Female Fluid Coupler 1130. A Seal 1121 encircling the Male Fluid Coupler Housing Top 1111 prevents fluid leaks from the junction of the Male Fluid Coupler 1110 and the Female Fluid Coupler 1130.

In some embodiments, the Male Fluid Coupler 1110 may couple with the Female Fluid Coupler 1130 and decoupled indefinitely through pushing the couplers together and pulling them apart. In some alternative embodiments, the coupling of the Male Fluid Coupler 1110 and the Female Fluid Coupler 1130 may require torsional force or oblique forces to couple or decouple.

As the Male Fluid Coupler 1110 and the Female Fluid Coupler 1130 slide further together, the Valve Stem 1321 of each coupler housing engage one another causing two Biasing Members 1124 and 1134 to compress. Compressing Biasing Members 1124 and 1134 permits the rest of Unitary Valves 1122 and 1132 to slide away from the coupling ends of coupling housings. As each Unitary Valve 1122 and 1132 slides away from the coupling end of coupling housings, Seals 1123 and 1133 separate from the Male Fluid Coupler Housing Top 1111 and Annulus 1144, respectively, opening a path for fluid to flow through. As stated earlier, the Seal 1121 seals the two housings prior to either unitary valve opening.

In some embodiments, Valve Stem 1321 includes an X-shaped cross section, which allows opposed valve stems to engage as intended with an increased amount of misalignment between the opposed valve stems while maintaining an adequate flow passage. Alternatively, in some embodiments other shapes of Valve Stem 1321 may be employed.

In some embodiments, Top Alignment Fins 1322 include a plurality of valve guides positioned on the ends of fins and configured to engage the interior wall of the cavity in coupler housing. Engaging the interior wall of cavity in coupler housing provides an alignment function for each Unitary Valve 1122 and 1132. The geometry of top alignment fins may be configured to provide a stabilizing function to each Unitary Valve 1122 and 1132, while minimizing the interference with fluid flow when the valve assembly is open.

The range of movement of each Biasing Members 1124 and 1134 of each Unitary Valve 1122 and 1132, respectively, is restricted in a predetermined range. Such restrictions prevent either one of the Biasing Members 1124 and 1134 in a coupler from being over compressed, preventing the opposing Unitary Valve 1122 or 1132 from opening. For example, if one biasing member is less stiff than the opposing biasing member, the enlarged portion of the top alignment fins will bottom out against either the Annulus 1144, or the narrow Bottom Opening 1215 of the Male Fluid Coupler Housing Top 1111, causing the stiffer biasing member to compress as Male Fluid Coupler 1110 and the Female Fluid Coupler 1130 are pressed further together. In this way, the other valve will fully unseat and open a flow path before Male Fluid Coupler 1110 is completely inserted into the Female Fluid Coupler 1130.

FIG. 11B shows a partially sectioned side view of the Fluid Coupler 1100 of FIG. 11A, shown in a disconnected configuration. In this figure, the Male Fluid Coupler Housing Top 1111 and the Male Fluid Coupler Housing Bottom 1112 are engaged. In some embodiments, the threading of the Male Fluid Coupler Housing Top 1111 may be screwed into the complimentary threading of the Male Fluid Coupler Housing Bottom 1112. The Biasing Member 1124 may sit within the Male Fluid Coupler Housing Bottom 1112, wherein the base of the Biasing Member 1124 rests on the constriction of the Male Fluid Coupler Housing Bottom 1112. Such an embodiment enables the Biasing Member 1124 to be compressed, without the Biasing Member 1124 slipping out of the male fluid coupler housing through the bottom of the Male Fluid Coupler Housing Bottom 1112.

The Unitary Valve 1122 rests upon the top base of the Biasing Member 1124. The Seal 1123 encircles the Unitary Valve 1122 by resting within the groove of the Unitary Valve 1122. In some embodiments, the bottom alignment fins of the Unitary Valve 1122 may rest within the resistive coils of the Biasing Member 1124 to ensure proper alignment of the Unitary Valve 1122 in relation to the Biasing Member 1124. In some embodiments, the regions around the groove of the Unitary Valve 1122 may be enlarged as to prevent the Unitary Valve 1122 from slipping below the top base of the Biasing Member 1124 and into the resistive coils.

In some embodiments, the Unitary Valve 1122 remains in the space created by the coupling of the Male Fluid Coupler Housing Top 1111 and the Male Fluid Coupler Housing Bottom 1112. In some embodiments, the Bottom of the Male Fluid Coupler Housing Top 1111 may be narrower and tapered than the rest of the cavity. Moreover, the enlargement of the top alignment fins of the Unitary Valve 1122 prevents the movement of the Unitary Valve 1122 further into the cavity of Male Fluid Coupler Housing Bottom 1112. Likewise, the enlarged groove of the Unitary Valve 1122 may prevent the Unitary Valve 1122 from extending too far into the cavity of the Male Fluid Coupler Housing Top 1111. Therefore, the Unitary Valve 1122 may slide longitudinally within the space created by the coupling of the Male Fluid Coupler Housing Top 1111 and the Male Fluid Coupler Housing Bottom 1112 with a predetermined and restrictive manner. The top alignment fins of the Unitary Valve 1122 may stabilize said movement of the Unitary Valve 1122.

In some embodiments, the Male Fluid Coupler 1110 may be assembled as to apply a longitudinally compressive force upon the Biasing Member 1124. As a result the resistive coils may apply upward pressure upon the Unitary Valve 1122, thus pushing the Unitary Valve 1122 upward and forcing the Seal 1123 encircling the Unitary Valve 1122 to come into contact with the tapered and narrower bottom opening of the Male Fluid Coupler Housing Top 1111. In doing so, the cavity is effectively blocked by the Unitary Valve 1122 and Seal 1123, thereby preventing fluid flow through the Male Fluid Coupler 1110.

In some embodiments, the Female Fluid Coupler 1130 may include a Receptacle 1141 on one end of its central cavity, and a Flow Valve 1143 on the opposite end of the central cavity. Under select circumstances, fluid may flow through the central cavity from the Receptacle 1141 end to the Flow Valve 1143. The Receptacle 1141 may be configured to receive the Male Fluid Coupler 1110. The Flow Valve 1143 may prevent backflow of the fluid through the Female Fluid Coupler 1130.

In some embodiments, the Female Fluid Coupler 1130 includes a Female Fluid Coupler Housing 1131, a Unitary Valve 1132, a Biasing Member 1134, a Seal 1133 and an Annulus 1144. Fluid Coupler Housing 1131 may be encircled by Barbs 1142, providing purchase for coupling of tubing to the Fluid Coupler Housing 1131. Tubing may be plastic, metal or alternate suitable material. Alternatively, in some embodiments, other methods of coupling tubing to the Female Fluid Coupler Housing 1131 may be utilized, such as glue, compression coupling or welding. Much like the Male Fluid Coupler 1110, in some embodiments, the Annulus 1144 may be screwed into the Female Fluid Coupler Housing 1131. The Biasing Member 1134 may sit within the Female Fluid Coupler Housing 1131, wherein the base of the Biasing Member 1134 rests on a constriction of the Female Fluid Coupler Housing 1131. Such an embodiment enables the Biasing Member 1134 to be compressed, without the Biasing Member 1134 slipping out of the Female Fluid Coupler Housing 1131 through the bottom opening of the Female Fluid Coupler Housing 1131.

The Unitary Valve 1132 rests upon the top of the Biasing Member 1134. The Seal 1133 encircles the Unitary Valve 1132 by resting within a groove of the Unitary Valve 1132. In some embodiments, the Unitary Valve 1132, Biasing Member 1134, and Seal 1133 may be identical to the Unitary Valve 1122, Biasing Member 1124, and Seal 1123 found in the Male Fluid Coupler 1110, for ease of manufacturing. Alternatively, different geometries or materials may be utilized to effectuate distinct purposes.

In some embodiments, the bottom alignment fins of the Unitary Valve 1132 may rest within the resistive coils of the Biasing Member 1134 to ensure proper alignment of the Unitary Valve 1132 in relation to the Biasing Member 1134. In some embodiments, the regions around the groove of the Unitary Valve 1132 may be enlarged as to prevent the Unitary Valve 1132 from slipping into the Biasing Member 1134.

In some embodiments, the Unitary Valve 1132 remains in the space created by the coupling of the Female Fluid Coupler Housing 1131 and the Annulus 1144. The Annulus 1144 may be narrower and more tapered than the cavity of the Female Fluid Coupler Housing 1131. The enlargement of the top alignment fins of the Unitary Valve 1132 prevents the movement of the Unitary Valve 1132 further into the cavity of Female Fluid Coupler Housing 1131. Likewise, the enlarged groove of the Unitary Valve 1132 may prevent the Unitary Valve 1132 from extending too far above the Annulus 1144. Therefore, the Unitary Valve 1132 may slide longitudinally within the space created by the coupling of the Annulus 1144 and the Female Fluid Coupler Housing 1131, within a predetermined and restrictive manner. The top alignment fins of the Unitary Valve 1132 may stabilize said movement of the Unitary Valve 1132.

In some embodiments, the Female Fluid Coupler 1130 may be assembled as to apply a longitudinally compressive force upon the Biasing Member 1134. As a result the Biasing Member 1134 may apply upward pressure upon the Unitary Valve 1132, thus pushing the Unitary Valve 1132 upward and forcing the Seal 1133 encircling the Unitary Valve 1132 to come into contact with the tapered and narrower Annulus 1144. In doing so, the cavity of the Female Fluid Coupler 1130 is effectively blocked by the Unitary Valve 1132 and Seal 1133, thereby preventing fluid flow through the Female Fluid Coupler 1130.

FIG. 12 shows a partially sectioned side view of a male Fluid Coupler Housing 1200 according to an embodiment of the present invention. The male Fluid Coupler Housing 1200 includes the Male Fluid Coupler Housing Top 1111 and Male Fluid Coupler Housing Bottom 1112. In some embodiments the Male Fluid Coupler Housing Top 1111 and Male Fluid Coupler Housing Bottom 1112 are two separate pieces, however, in some alternate embodiments they may be conjoined or of a single piece.

The Male Fluid Coupler Housing Top 1111 includes a Top Opening 1211, which enabled fluid to flow through the center of the Male Fluid Coupler Housing Top 1111 to the Bottom Opening 1215 through a cavity. In some embodiments, the Bottom Opening 1215 may be narrower and tapered than the rest of the cavity. Additionally, in some embodiments, an Outer Ridge 1212 and an Inner Ridge 1213 may encircle the circumference of the Male Fluid Coupler Housing Top 1111. A groove may exist between the Outer Ridge 1212 and the Inner Ridge 1213. The base of the Male Fluid Coupler Housing Top 1111 may include helical Threads 1214 for coupling the Male Fluid Coupler Housing Top 1111 to the remainder of the male fluid coupler housing. Alternatively, in some embodiments, other fastening methods, such as welding, compression fitting or glue may be utilized to attach the Male Fluid Coupler Housing Top 1111 to the remainder of the male fluid coupler housing.

The Male Fluid Coupler Housing Bottom 1112 may include a Top Opening 1221 which enabled fluid to flow through the center of the Male Fluid Coupler Housing Bottom 1112 to the Bottom Opening 1225 through a cavity. The Top Opening 1221 may include helical threading for receiving the Male Fluid Coupler Housing Top 1111. As stated earlier, other fastening methods, such as welding, compression fitting or glue may be utilized to attach the Male Fluid Coupler Housing Top 1111 to the Male Fluid Coupler Housing Bottom 1112.

In some embodiments, a Ridge 1222 may encircle the circumference of the Male Fluid Coupler Housing Bottom 1112. Additionally, in some embodiments, one or more wedge shaped ridges, or Barbs 1223, may encircle the circumference of the Male Fluid Coupler Housing Bottom 1112 providing purchase for coupling of tubing to the Fluid Coupler Housing Bottom 1112. Tubing may be plastic, metal or alternate suitable material. Alternatively, in some embodiments, other methods of coupling tubing to the Male Fluid Coupler Housing Bottom 1112 may be utilized, such as glue, compression coupling or welding.

In some embodiments, the interior cavity of the Male Fluid Coupler Housing Bottom 1112 may narrow at a Constriction 1224. Such a Constriction 1224 may be utilized to restrain a Biasing Member 1124 within the male fluid coupler housing.

FIG. 13 shows an exploded assembly view of the Male Fluid Coupler 1110 according to an embodiment of the present invention. The Male Fluid Coupler 1110 includes the coupler housings, including the Male Fluid Coupler Housing Top 1111 and the Male Fluid Coupler Housing Bottom 1112, a Unitary Valve 1122, the Biasing Member 1124, and two Seals 1121 and 1123. Seals 1121 and 1123 may be integrated into the Male Fluid Coupler 1110, or in some embodiments may be separate components. In some of these embodiments, Seals 1121 and 1123 may include rubber O-type rings, polytetrafluoroethylene washers, or any other suitable sealer.

The Biasing Member 1124 may be a helical spring, ribbon spring, piston or any other member capable of exerting force. Additionally, in some embodiments, the Biasing Member 1124 may include a metal, plastic or any other suitable material. In some embodiments, the Biasing Member 1124 may include Bases 1341 and 1343. Resistive Coils 1342 of the Biasing Member 1124 may exert an outward longitudinal force against the Bases 1341 and 1343 when under a compressive force.

The Unitary Valve 1122 may include a Valve Stem 1321. Top Alignment Fins 1322 and Bottom Alignment Fins 1324 are coupled to the Valve Stem 1321 to ensure that the Unitary Valve 1122 remains stable within the coupler housing. Additionally, in some embodiments, a Groove 1323 may exist between the Top Alignment Fins 1322 and Bottom Alignment Fins 1324.

FIG. 14 shows a sectional side view of the Fluid Circuit Connection System 1400 including the Fluid Coupler 1100 of FIG. 11A, according to an embodiment of the present invention. Although useful for a variety of fluid circuit systems, the illustrated embodiment is shown in the context of a contrast therapy wrap. Fluid Circuit Connection System 1400 includes an Object Fitting 1410, which may be connected to a contrast therapy applicator, such as a pad or wrap. The Contrast therapy applicator may be any of a variety of contrast therapy applicators including arm wraps, leg wraps, waist wraps, shoulder wraps, and pads for applying therapy to various sore body parts. Object Fitting 1410 may be configured to receive a Quick-Release Connector 1430 attached to one end of a Set of Tubes 1440. At the other end of Tube Set 1440 is another Quick-Release Connector 1450 configured to connect to a Source Fitting 1460. Source Fitting 1460 connects the fluid circuit to a source of hot and cold fluid for circulation.

It will be understood that in the illustrated embodiment both Quick-Release Connectors 1410 and 1450 may be used to attach to either Object Fitting 1410 or Source Fitting 1460. Other embodiments of the present invention may have Quick-Release Connectors 1410 and 1450 that may be fitting specific. For example, a quick-release connector configured to attach to Object Fitting 1410 may not connect to Source Fitting 1460 and vice versa. This may be desirable for enabling the use of a contrast therapy fluid supply with a variety of therapy wraps and pads that may have different types and or sizes of object fittings.

The Object Fitting 1410 may include a Housing 1411, Fluid Channels 1412, a Female Fluid Coupler 1130a and Male Fluid Coupler 1110a. The Fluid Channels 1412 may include plastic or rubber tubing, or may be integrated into the Housing 1411. The Housing 1411 may be injection molded, carved, compacted with sintering, rotational molded, thermoformed, or any other suitable manufacturing process. Additionally, the Housing 1411 may be plastic, metal, ceramic, wood or any other suitable material.

The Object Fitting 1410 may be coupled with the Quick-Release Connector 1430 along the illustrated Path 1420. The Quick-Release Connector 1430 includes a Housing 1431, Fluid Channels 1442, a Female Fluid Coupler 1130b and Male Fluid Coupler 1110b. It may be seen that the Female Fluid Coupler 1130b engages the Male Fluid Coupler 1110a located on the Object Fitting 1410; and likewise, the Male Fluid Coupler 1110b is engaged by the Female Fluid Coupler 1130a located on the Object Fitting 1410. Such a coupling arrangement ensures proper fitting and correct fluid directional flow. The Housing 1431 may be injection molded, carved, compacted with sintering, rotational molded, thermoformed, or any other suitable manufacturing process. Additionally, the Housing 1431 may be plastic, metal, ceramic, wood or any other suitable material.

The Fluid Channels 1442 may include plastic or rubber tubing, or may be integrated into the Housing 1431. The Fluid Channels 1442 may exit the Housing 1431 and extend any desired distance, as illustrated at 1441. Tube Set 1440 includes the Fluid Channels 1442, extending along 1441. In the Tube Set 1440, the Fluid Channels 1442 may be fused together, or may be surrounded by a common sheath, as to minimize the possibility of tangles and general visual clutter.

The Fluid Channels 1442 enter the Quick-Release Connector 1450. The Quick-Release Connector 1450 includes a Housing 1451, Fluid Channels 1442, a female fluid coupler and male fluid coupler. The female fluid coupler and male fluid coupler may be seen engaging their complementary male fluid coupler and female fluid coupler, respectively, located in the Source Fitting 1460, resulting in Joined Fluid Couplers 1100. The Housing 1451 may be injection molded, carved, compacted with sintering, rotational molded, thermoformed, or any other suitable manufacturing process. Additionally, the Housing 1451 may be plastic, metal, ceramic, wood or any other suitable material. Moreover, the Fluid Channels 1442 may include plastic or rubber tubing, or may be integrated into the Housing 1451.

Although the present invention has been described in considerable detail with reference to exemplary embodiments, modifications and variations may be made to the disclosed embodiments while remaining within the subject and spirit of the invention. Therefore, the spirit and scope of the appended claims should not be limited to the description of the versions contained herein.

What is claimed is:

1. A quick release fluid connector, useful in association with a fluidic circuit, the quick release fluid connector comprising:

a male coupler, having an elongated longitudinal axis, wherein the male coupler includes a segmented male housing, wherein the segmented male housing further comprises:

a top housing unit including a top central cavity, and a tapered opening;

a bottom housing unit configured to couple to the top housing unit, including a bottom central cavity, and a constriction in the bottom central cavity, wherein the top housing unit coupled to the bottom housing unit aligns the top central cavity and the bottom central cavity along the longitudinal axis generating a first central cavity;

and a first unitary valve and a first biasing member within the first central cavity, wherein the first unitary valve is configured to dynamically position longitudinally within the first central cavity, and wherein the first unitary valve includes:
- top alignment fins extending from the top portion of the first unitary valve configured to align the first unitary valve within the first central cavity when the first unitary valve is dynamically positioned, wherein the top alignment fins include an enlarged portion configured to restrict positioning of the top alignment fins below the first central cavity, thereby limiting the depth the first unitary valve is able to dynamically position longitudinally within the first central cavity;
- bottom alignment fins extending from the bottom portion of the first unitary valve configured to align the first unitary valve in relation to the coupled first biasing member when the first unitary valve is dynamically positioned; and
- a groove configured to receive a first sealer, wherein the groove is located between the top alignment fins and the bottom alignment fins;

a female coupler configured to receive the male coupler, having an elongated longitudinal axis, wherein the female coupler includes a segmented female housing; and a seal configured to be positioned between the male coupler and the female coupler when they are coupled, preventing fluid from leaking out from the coupled fluid coupler.

2. The quick release fluid connector of claim 1, wherein the top housing unit of the segmented male housing includes threading, and further wherein the bottom housing unit of the segmented male housing includes threading.

3. The quick release fluid connector of claim 2, wherein the top housing unit of the segmented male housing couples to the bottom housing unit of the segmented male housing by screwing together the threading of the top housing unit and the threading of the bottom housing unit.

4. The quick release fluid connector of claim 1, wherein the top housing unit of the segmented male housing couples to the bottom housing unit of the segmented male housing by at least one of compression fitting, glue and welding.

5. The quick release fluid connector of claim 1, wherein the first biasing member engages the first unitary valve and the constriction of the bottom housing unit.

6. The quick release fluid connector of claim 5, wherein the first biasing member is a spring.

7. The quick release fluid connector of claim 1, wherein the segmented female housing further comprises:
- an annulus including a top central cavity, and a tapered opening; and
- a housing unit configured to couple to the annulus, including a bottom central cavity, and a constriction in the bottom central cavity.

8. The quick release fluid connector of claim 7, wherein the annulus of the segmented female housing includes threading, and further wherein the housing unit of the segmented female housing includes threading.

9. The quick release fluid connector of claim 8, wherein the annulus of the segmented female housing couples to the housing unit of the segmented female housing by screwing together the threading of the annulus and the threading of the housing unit.

10. The quick release fluid connector of claim 7, wherein the annulus of the segmented female housing couples to the housing unit of the segmented female housing by at least one of compression fitting, glue and welding.

11. The quick release fluid connector of claim 9, wherein the annulus coupled to the housing unit aligns the top central cavity and the bottom central cavity along the longitudinal axis generating a second central cavity, and wherein the annulus coupled to the housing unit enables reception of a second unitary valve and a second biasing member within the second central cavity.

12. The quick release fluid connector of claim 11, wherein the second biasing member engages the second unitary valve and the annulus of the housing unit.

13. The quick release fluid connector of claim 12, wherein the second biasing member is a spring.

14. The quick release fluid connector of claim 12, wherein the second unitary valve is configured to dynamically position longitudinally within the second central cavity, and wherein the range of movement of dynamic positioning of the second unitary valve is configurable.

15. The quick release fluid connector of claim 14, wherein the second unitary valve includes:
- top alignment fins extending from the top portion of the second unitary valve configured to align the second unitary valve within the second central cavity when the second unitary valve is dynamically positioned, wherein the top alignment fins include an enlarged portion configured to restrict positioning of the top alignment fins within the second central cavity, thereby limiting the depth the second unitary valve is able to dynamically position longitudinally within the second central cavity;
- bottom alignment fins extending from the bottom portion of the second unitary valve configured to align the second unitary valve in relation to the coupled second biasing member when the second unitary valve is dynamically positioned; and
- a groove configured to receive a second sealer, wherein the groove is located between the top alignment fins and the bottom alignment fins.

16. The quick release fluid connector coupler of claim 1, wherein the fluid coupler is configured to be in one of a coupled position and an uncoupled position, wherein in the coupled position a first unitary valve and a second unitary valve are open, permitting fluid flow through the fluid coupler, and in the uncoupled position the first unitary valve and the second unitary valve are closed preventing fluid leakage.

* * * * *